United States Patent [19]
Mays

[11] Patent Number: 5,636,991
[45] Date of Patent: *Jun. 10, 1997

[54] STORAGE AND MOUNTING DEVICE FOR A DENTAL RETENTIVE PIN

[76] Inventor: Ralph C. Mays, 5436 S. Mingo Rd., Tulsa, Okla. 74146

[ * ] Notice: The term of this patent shall not extend beyond the expiration date of Pat. No. 5,409,377.

[21] Appl. No.: 426,821

[22] Filed: Apr. 21, 1995

Related U.S. Application Data

[63] Continuation-in-part of Ser. No. 194,844, Feb. 14, 1994, Pat. No. 5,409,377.
[51] Int. Cl.$^6$ .................................................. A61C 5/08
[52] U.S. Cl. ................................... 433/220; 206/368
[58] Field of Search ...................... 433/173, 174, 433/175, 220, 221, 225; 206/63.5, 368

[56] References Cited

U.S. PATENT DOCUMENTS

| | | |
|---|---|---|
| 3,378,925 | 4/1968 | Faller ........................... 433/26 |
| 3,579,306 | 5/1971 | Crane . |
| 3,703,977 | 11/1972 | Pisarek ........................... 221/213 |
| 3,890,204 | 6/1975 | Avery ........................... 195/139 |
| 4,220,712 | 9/1980 | Staffolani ........................ 433/173 |
| 4,364,473 | 12/1982 | Bogaert .......................... 206/63.5 |
| 4,445,611 | 5/1984 | Shofu ............................ 206/369 |
| 4,856,648 | 8/1989 | Krueger ......................... 206/63.5 |
| 5,062,800 | 11/1991 | Niznick ......................... 433/229 |

FOREIGN PATENT DOCUMENTS 427181  8/1911  France .

*Primary Examiner*—Cary E. O'Connor
*Attorney, Agent, or Firm*—Head, Johnson & Kachigian

[57] ABSTRACT

A combined storage container and installation device for a dental retentive pin. The storage container is elongated and has a top opening. A cap has a recess therein to hold the proximal end of the dental retentive pin while allowing fluid to pass into and through the recess. The cap is received and held in the open top of the container. By holding and manipulating the cap, the dental retentive pin may be removed from the container and installed under sterilized conditions without the user touching the pin.

17 Claims, 2 Drawing Sheets

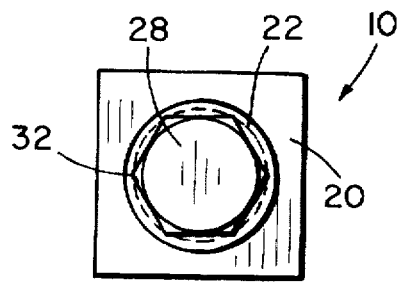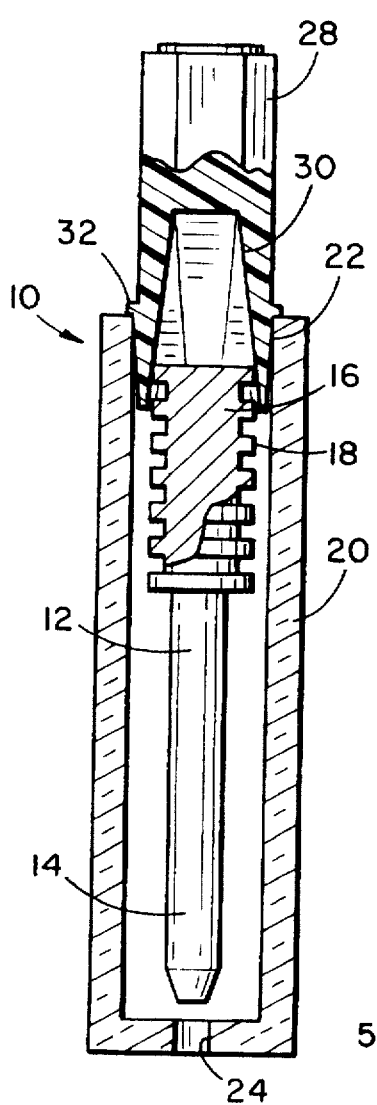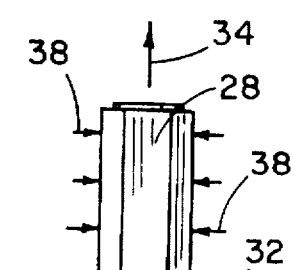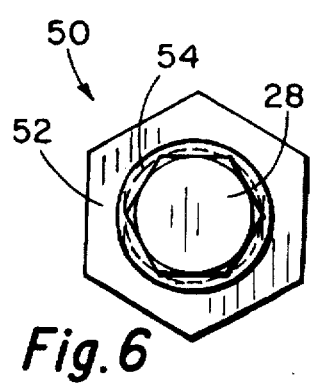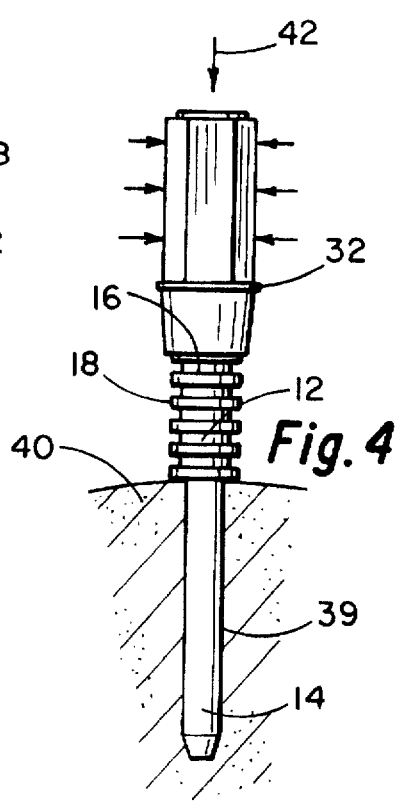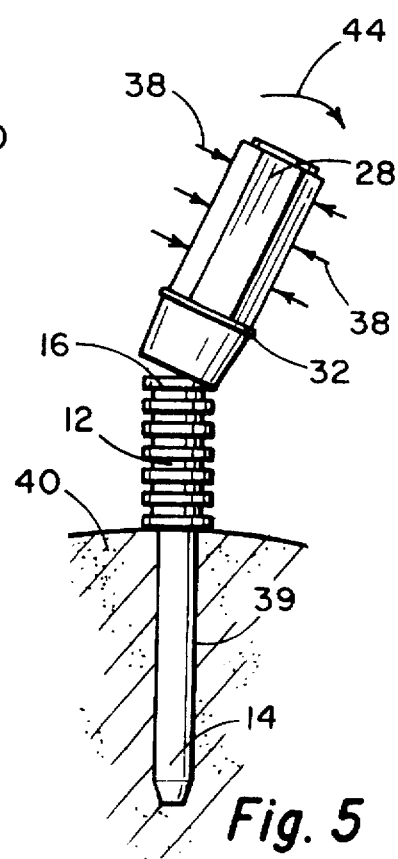

STORAGE AND MOUNTING DEVICE FOR A DENTAL RETENTIVE PIN

CROSS-REFERENCE TO RELATED APPLICATIONS

This is a continuation-in-part application of U.S. patent application Ser. No. 08/194,844 filed 14 Feb. 1994, now U.S. Pat. No. 5,409,377, issued Apr. 25 1995.

BACKGROUND OF THE INVENTION

Reference To A Microfiche Appendix

This application is not referenced in a microfiche appendix.

1. Field of the Invention

The present invention relates to a combined storage and installation device for a dental retentive pin. In particular, the present invention relates to a container to receive and hold a dental retentive pin wherein the dental retentive pin may be subsequently removed from the container and installed in a patient without contamination.

2. Prior Art

Dental posts and/or dental retentive pins are widely used for securing a dental device, such as a crown or the like, to a tooth. In certain instances, the human tooth is chipped or worn away so that the crown is difficult to secure to the natural tooth. To securely support a dental device, such as a crown, onto a natural tooth, a pin or post is embedded into an opening made in the tooth so that a portion of the pin or post extends externally from the tooth and serves as reinforcement for receiving a crown.

In mounting a dental post or retentive pin into a natural tooth, a dentist bores a hole of selected diameter generally following the tooth's root canal. The bore hole is drilled from the tooth's external surface into the tooth. The dental post or retentive pin is thereafter inserted into the hole.

Contamination of the dental post or retentive pin can quickly lead to infection. Additionally, some types of dental posts or retentive pins have a composite material on the stem; touching or handling of the dental post decreases the integrity of the dental post or retentive pin. As an example, oil from human fingers on the surface of the post or pin decreases the ability to bond the tooth.

The dental post or pin must be packaged and transported under sterile conditions and then installed in the patient under sterile conditions. Alternatively, the dental post or pin may be sterilized immediately prior to installation in the tooth.

Various types of packaging have been used in the past for dental posts or pins. As an example, Krueger, U.S. Pat. No. 4,856,648, identifies the problem of possible contamination. Krueger recesses a socket in the head of the dental post to secure a cap thereto. This arrangement requires a special dental post with a recessed socket. Additionally, the socket itself is not sterilized with the cap inserted.

There remains a need for a combined storage container to retain and store standard dental posts and retentive pins and to also be used as an installation device when installing in a patient.

It is, therefore, a principal object and purpose of the present invention to provide a combined storage container to hold and store a dental post or dental retentive pin and allow sterilization of the dental post or pin without handling or contamination of the dental post.

It is a further object and purpose of the present invention to provide a combined storage and sterilization container which will allow sterilization of the entire dental post or retentive pin.

It is a further object and purpose of the present invention to provide a cap which acts as a handle to retain, move and install a dental post or retentive pin.

While the above discussions relating to the prior art have been made in relationship to a "dental post", it is understood that the prior art relating to dental posts is relevant to dental retentive pins of the type which is the subject of the present disclosure.

SUMMARY OF THE INVENTION

The present invention provides a combined storage and container and installation device for a dental post or dental retentive pin.

A dental post or pin, including an elongated distal end and a proximal end, may be stored within the container of the device. The elongated container, which receives the entire dental post or pin therein, includes a top opening larger than the diameter of the dental post or pin. The interior diameter of the container is at all places larger than the diameter of the dental post or pin.

A somewhat elongated cap has a recess at one end. The recess is slightly tapered so that its widest point is at the surface of the cap. The recess receives and holds the proximal head of the dental post or proximal end or a retentive pin by frictional engagement. When the cap is engaged over the proximal head or proximal end, the axis of the cap is aligned with the axis of the dental post or pin.

The cap is, in turn, receivable in the top opening of the container. The exterior of the cap engages the interior wall of the container so that the cap is retained in the open top of the container. An eternally extending flange can be employed on the cap to act as a stop to prohibit the cap from being inserted past a pre-determined point.

In one embodiment, the proximal head of a dental post or proximal end of retentive pin does not form a seal with the recess of the cap. Accordingly, while the dental post or pin may be wedged and retained in the cap recess, fluid will be able to pass into and through the recess.

In order to utilize the device, initially the distal end of the dental post or pin is inserted and received within the recess of the cap. Thereafter, movement or manipulation of the cap will move or manipulate the dental post or pin.

The sterilization process may then be performed through any known process.

The cap and accompanying dental post or pin are placed into the container through the open top with the distal end inserted first into the container. The cap is then wedged into the opening of the top of the container so that the dental post or pin is thereby suspended inside the container.

The dental post or pin may be sterilized using any known sterilization procedure. Gamma ray sterilization may be performed while the post or pin is in the container. Gas, steam or other fluid may be used to surround the device and pass through the additional opening. Additionally, fluid will be allowed to move into and through the recess in the cap in order to sterilize the post or pin.

The dental post or pin may be stored and transported in the container without contamination until the dental post or pin is ready for insertion in a patient. The cap and accompanying post or pin are then separated from the container by moving the cap in an opposite direction from the elongated container. The dental post or pin is thus moved and manipulated without touching or otherwise contaminating the post or pin.

Thereafter, the dental post or pin is inserted into a pre-arranged or pre-drilled opening in a tooth. Again, the cap securely holds the dental post or pin so that moving the cap will also translate to movement of the dental post or pin. Finally, once the dental post or pin is secured within the opening in the tooth, the cap may be separated from the dental post or pin. While holding the exterior of the cap, the axis of the cap will be brought out of alignment with the axis of the dental post or pin. The frictional engagement between the proximal head of the post or proximal end of the pin and the recess will thereby be broken. The entire installation procedure is, thus, performed without handling or touching of the dental post or pin.

BRIEF DESCRIPTION OF THE DRAWINGS

FIG. 1 illustrates a combined storage and sterilization container and installation device for a dental post constructed in accordance with the present invention which is partially cut-away to reveal the dental post held therein.

FIG. 2 is a top plan view of the combination device shown in FIG. 1.

FIGS. 3, 4, and 5 illustrate sequentially the process to remove a dental post from the combined device of the present invention and to install it in a patient's tooth.

FIG. 6 is a top plan view of an alternate embodiment of the combined storage and sterilization container and installation device constructed in accordance with the present invention.

DETAILED DESCRIPTION OF THE PREFERRED EMBODIMENTS

Figure 7:
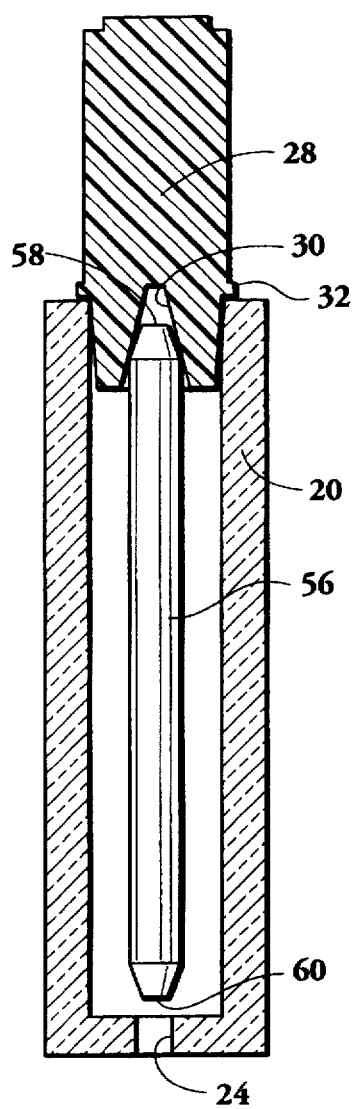
FIG. 7 is a cross-sectional elevational view showing the storage container and cap supporting a dental retainer pin. In the arrangement of FIG. 7, the retainer pin within the container may be shipped, stored and, prior to use, sterilized.

Referring to the drawings in detail, FIG. 1 shows a combined storage container and installation device 10 of the present invention partially cut-away. A dental post 12, partially cut away, is stored within the combined device 10 shown in FIG. 1. The dental post 12 includes an elongated distal end 14 and a proximal head 16. After installation in a patient, the distal end is embedded in an opening which is drilled into a tooth while the proximal head extends therefrom. The proximal head is thereafter used to secure a crown or other dental device.

The dental post 12 of the present embodiment includes a series of extending parallel flanges 18 at the head 16. It will be recognized that dental posts of other configurations might be utilized with the present invention.

An elongated container 20 receives the entire dental post 12 therein. The elongated container is, thus, longer than the length of the dental post. The elongated container 20 includes a top opening 22 larger than the diameter of the dental post 12. In the present embodiment, the container 20 also includes an additional opening 24 opposed to the top opening. As will be seen herein, the interior diameter of the container 20 is at all places larger than the diameter of the dental post 12 so that the dental post does not touch the interior of the container.

A cap 28 is received in the open top 22. The caps may be colored coded to identify different size posts. In FIG. 1, the cap 28 is partially cut away for clarity. The cap 28 is somewhat elongated and has a recess 30 at one end. The recess 30 is slightly tapered so that its widest point is at the surface of the cap 28. In the present embodiment, the recess is tapered at approximately 7°. The recess receives and holds the proximal head 16 of the dental post by frictional engagement. When the cap is engaged over the proximal head, the axis of the cap 28 is aligned with the axis of the dental post 12.

A cap 28 is, in turn, receivable in the top opening 22 of the container as seen in FIG. 1.

The exterior of the cap 28 engages the top opening of the container 20 so that the cap is retained in the open top 22 of the container. An externally extending flange 32 acts as a stop to prohibit the cap 28 from being inserted into the container past a certain maximum point.

With reference to the top plan view shown in FIG. 2 and continuing reference to FIG. 1, it will be observed that while the proximal head 16 is substantially cylindrical, the cap recess 30 is neither cylindrical nor frusto-conical. The recess has flat walls so that the recess is square in cross-section. The proximal head does not, thus, form a seal with the recess. Accordingly, while the dental post 12 may be wedged and retained in the recess, fluid will be able to pass into and through the recess.

Alternatively, the recess might be frusto-conical.

FIG. 2 illustrates a top plan view of the device. FIGS. 1, 3, 4 and 5 illustrate a typical sequential procedure to store a dental post and thereafter install the dental post in a patient. Initially, the proximal end of the dental post is inserted and received within the recess 30 of the cap 28. Once the proximal head is inserted into the recess, movement or manipulation of the cap will move or manipulate the dental post.

The dental post may be sterilized using known sterilization procedures, such as gamma ray sterilization, while the post is in the container. Alternatively, the cap and post may be removed from the container. Gas, steam or other fluid will be allowed to surround the post. Accordingly, the fluid will surround and move past the dental post 12. Additionally, fluid will be allowed to move into and through the recess 30 in the cap. In this manner, the entire dental post may be sterilized.

As seen in FIG. 1, the cap and dental post are then placed into the container through the open top 22. The distal end 14 is inserted first into the container. The cap 28 then wedges into the open top 22 of the container. It will be observed that the dental post is thereby suspended within the container.

Once the dental post is ready for insertion in a patient, the cap is then separated from the container by moving the cap in an opposite direction from the elongated container 20 as illustrated by arrows 34 and 36. This may be accomplished by grasping in one hand the end of the cap at arrows 38 while grasping the container in the other hand. It will be observed that the dental post 12 is thus moved and manipulated without touching or otherwise contaminating the dental post.

Thereafter, as shown in FIG. 4, the dental post is inserted into a prearranged or pre-drilled opening 39 in a tooth 40.

Arrow 42 indicates the movement of the cap. Again, the cap securely holds the dental post so that moving the cap will translate to movement of the dental post.

Finally, as seen in FIG. 5, once the dental post is secured within the tooth opening 39, the cap 28 may be separated from the dental post. While holding the cap 28 at arrows 38, the axis of the cap will be brought out of alignment with the axis of the dental post 12, as best illustrated by arrow 44 in FIG. 5. The entire installation procedure has, thus, been performed without handling or touching the dental post.

FIG. 6 illustrates a top plan view of an alternate embodiment of the combined device 50. The exterior of the container 52 is hexagon in cross-section rather than square. While the exterior of the container may take other shapes, a non-cylindrical shape has been found advantageous to prevent the container 20 from rolling if placed on its side. The open top of container 52 is indicated by the numeral 54.

Figure 8:
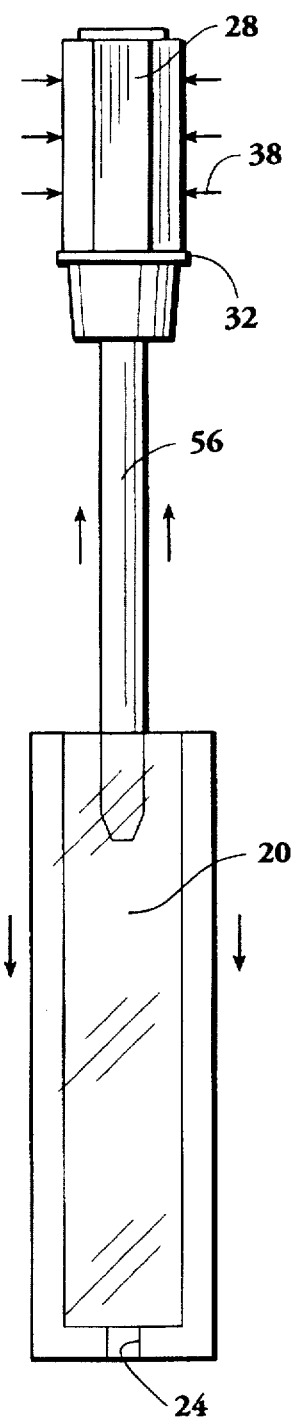
FIG. 8 shows the cap having the retainer pin attached to it being removed from the container.
Figure 9:
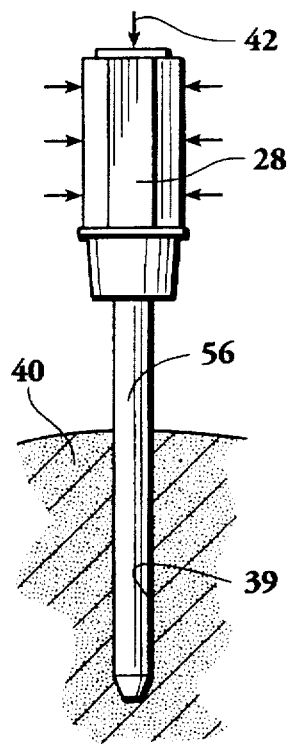
FIG. 9 shows the retainer pin inserted into a drilled hole in a tooth of a patient by use of the cap and without it being necessary to touch the retainer pin.
Figure 10:
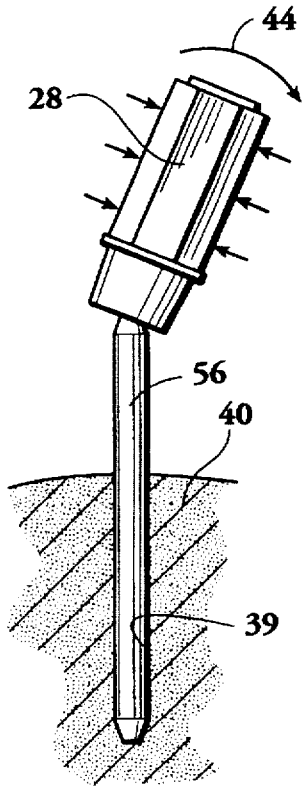
FIG. 10 shows the cap being removed from the retainer pin without requiring upward force on the cap relative to the retainer pin.

FIGS. 7 through 10 show a slightly alternate embodiment of the invention. The invention as heretofore described is completely applicable in ever respect to the embodiment of FIGS. 7 through 10, the only difference being that in FIGS. 7 through 10 instead of a dental post having a proximal head, the invention is illustrated as it is applicable to a dental retentive pin. Dental posts are typically installed in a central position within a tooth, such as, after an endodontic procedure in which the post can penetrate or encompass the root canal. Dental retentive pins are relatively smaller and are typically embedded in teeth at locations spaced away from the root canal area. In this way, retentive pins can be installed in a tooth having a live root canal. A retentive pin 56 is illustrated as being the type that is cylindrical and has a proximal end 58 and a distal end 60. While the retentive pin 56 is illustrated as being cylindrical, some retentive pins have an irregular external surface, such as provided by threaded or circumferential flutes. Irrespective of its external surface, the typical retentive pin is elongated, straight, generally cylindrical with a distal end and proximal end. It is understood that the external configuration of the retentive pin is not relevant to this invention and that the invention can be used with retentive pins of any known external configuration.

The proximal end 58 of retentive pin 56 is removably retained by cap member recess 30 in exactly the same way as previously described, the only difference being that when the apparatus is used for a retentive pin, the container 20 and cap 28 can be dimensionally smaller.

The technique for removing a retentive pin 56 from container 20, inserting it into a drilled hole 39 in a tooth 40 and disconnecting the cap 28 from retentive pin 56 is carried out in the same way as previously described wherein the device is used to support a dental post.

Further, the internal configuration of recess 30 is preferably made to be non-circular in cross-sections and, more particularly, non-conical so that it is possible for sterilizing fluids to pass into the recess 30 even as the recess removably retains the proximal end 58 of a dental retentive pin 56.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A combined storage container and installation device for a dental retentive pin, the pin having a distal end and a proximal end, the distal end being receivable in a drilled hole in a tooth in the mouth of a patient, which device comprises:

an elongated container to receive the dental retentive pin therein, said container having a top opening;

a cap having a recess configured and dimensioned to receive and releasably hold said proximal end of said dental retentive pin, said cap being receivable in said top opening for storage of said dental retentive pin in said elongated container, said cap being configured and dimensioned to be manually manipulatable in the mouth of a patient so that said dental retentive pin may be removed from said container and installed in a drilled hole in the tooth of a patient while holding said cap and without touching said dental retentive pin, said cap being detachable from said dental retentive pin by pivotation of said cap relative to said dental retentive pin with substantially no pulling action between said cap and said dental retentive pin being required.

2. A device as set forth in claim 1 wherein said proximal end of said dental retentive pin is substantially cylindrical and said cap recess is neither cylindrical nor frusto-conical in order to allow fluid to pass into and through said recess while said proximal end is held therein.

3. A device as set forth in claim 1 wherein said dental retentive pin may be sterilized while in said container.

4. A device as set forth in claim 1 wherein said elongated container has an interior larger in diameter than the diameter of said dental retentive pin.

5. A device as set forth in claim 1 wherein said cap recess is tapered.

6. A device as set forth in claim 5 wherein said recess is tapered at approximately 7°.

7. A device as set forth in claim 1 including at least one additional opening in said container to allow fluid to pass into and through said container.

8. A device as set forth in claim 1 wherein the axis of said dental retentive pin and the axis of said cap are aligned during installation and wherein said cap is moved out of alignment to separate said dental retentive pin from said cap.

9. A combined storage and sterilization container and installation device which device comprises:

an elongated container having a top opening;

a cap removably receivable in said container top opening and having a recess therein;

means to receive and hold said proximal end of said dental retentive pin in said cap recess while allowing sterilizing fluid to pass into said recess to thereby surround said dental retentive pin proximal end; and means to install said dental retentive pin by holding and manipulating said cap in order to install said dental retentive pin under sterilized conditions.

10. A combined device as set forth in claim 9 including means to allow sterilizing fluid to pass into and through said container and into said recess in said cap while said cap is in said container top opening.

11. A combined device as set forth in claim 10 wherein said proximal end is substantially cylindrical and said cap recess is neither cylindrical nor frusto-conical.

12. A combined device as set forth in claim 9 wherein said means allowing sterilizing fluid to pass into said recess in said cap includes said recess not being circular and said dental retentive pin being cylindrical.

13. A combined device as set forth in claim 12 wherein said cap recess is tapered at approximately 7°.

14. A combined device as set forth in claim 9 wherein said cap recess is tapered.

15. A method of storing, sterilizing, and installing a dental retentive pin having a distal end and a proximal end, which method comprises:

receiving and holding said proximal end in a recess in a cap, the recess being configured to permit the flow of sterilizing fluid therein while holding said dental retentive pin proximal end;

inserting said cap and dental retentive pin in an elongated container;

receiving and holding said cap in an open top in said container, said container having an aperture therein;

sterilizing said dental retentive pin by passing sterilizing fluid into said container and into said recess so that thereby said sterilizing fluid surrounds the entirety of said dental retentive pin including said proximal end;

removing said dental retentive pin from said container by holding and manipulating said cap; and installing said dental retentive pin in said patient without touching said dental post.

16. A method of storing, sterilizing and installing a dental retentive pin according to claim 15 wherein said last mentioned step of installing said dental retentive pin in said patient without touching said dental retentive pin includes the step of detaching said cap from said dental retentive pin by pivotation of said cap relative to said dental retentive pin with substantially no pulling action between said cap and said dental retentive pin.

17. A method of storing and installing a dental retentive pin into a drilled hole in a tooth in the mouth of a patient, the dental retentive pin having a distal end and a proximal end, which method comprises:

receiving and holding said proximal end in a tapered recess in a cap, the cap being configured and dimensioned to be manually manipulatable in the mouth of a patient;

inserting said cap and dental retentive pin in the open top of an elongated container for shipment and/or storage;

removing said dental retentive pin from said container by holding and manipulating said cap; and installing said dental pin in a drilled hole in a tooth in the mouth of a patient by manually manipulating said cap without handling said dental retentive pin, said cap then being detachable from said dental retentive pin by pivotation of said cap relative to said dental retentive pin with substantially no pulling action between said cap and said dental retentive pin being required.

\* \* \* \* \*

UNITED STATES PATENT AND TRADEMARK OFFICE
CERTIFICATE OF CORRECTION

PATENT NO. : 5,636,991
DATED : June 10, 1997
INVENTOR(S) : Ralph C. MAYS

It is certified that error appears in the above-indentified patent and that said Letters Patent is hereby corrected as shown below:

Column 2, line 36, delete "eternally" and substitute --externally-- therefor; and Column 6, line 52 (line 2 of claim 9), after "device" and before "which", insert --for a dental retentive pin, the dental retentive pin having a distal end and a proximal end,--.

Signed and Sealed this

Second Day of September, 1997

Attest:

BRUCE LEHMAN

Attesting Officer

Commissioner of Patents and Trademarks